US005849515A

United States Patent [19]
Grant

[11] Patent Number: 5,849,515
[45] Date of Patent: *Dec. 15, 1998

[54] **METHOD AND MEDIUM FOR USE IN DETECTING *E. COLI* AND TOTAL COLIFORMS**

[75] Inventor: Michael A. Grant, Ames, Iowa

[73] Assignee: Hach Company, Ames, Iowa

[*] Notice: The term of this patent shall not extend beyond the expiration date of Pat. No. 5,650,290.

[21] Appl. No.: 790,195

[22] Filed: Jan. 30, 1997

Related U.S. Application Data

[63] Continuation-in-part of Ser. No. 526,865, Sep. 12, 1995, Pat. No. 5,650,290, which is a continuation-in-part of Ser. No. 221,831, Apr. 1, 1994, abandoned.

[51] Int. Cl.$^6$ ....................................................... C12Q 1/04
[52] U.S. Cl. .................................. 435/34; 435/4; 435/29; 435/38; 435/39; 435/252.1; 435/252.8; 435/253.6; 435/848; 435/843
[58] Field of Search .................................. 435/4, 34, 29, 435/38, 35, 252.1, 252.8, 253.6, 848, 845, 39

[56] References Cited

U.S. PATENT DOCUMENTS

| | | | |
|---|---|---|---|
| 3,496,066 | 2/1970 | Berger et al. | 195/103.5 |
| 3,551,295 | 12/1970 | Dyer | 195/103.5 |
| 3,870,601 | 3/1975 | Warren et al. | 195/103.5 R |
| 4,070,247 | 1/1978 | Burt | 195/100 |
| 4,129,483 | 12/1978 | Bochner | 195/100 |
| 4,242,447 | 12/1980 | Findl et al. | 435/39 |
| 4,245,043 | 1/1981 | Lund | 435/36 |
| 4,288,543 | 9/1981 | Sielaff et al. | 435/34 |
| 4,308,348 | 12/1981 | Monget | 435/38 |
| 4,318,916 | 3/1982 | Okamura et al. | 514/210 |
| 4,388,233 | 6/1983 | Bissell et al. | 260/112.5 R |
| 4,812,409 | 3/1989 | Babb et al. | 436/7 |
| 4,923,804 | 5/1990 | Ley et al. | 435/38 |
| 4,925,789 | 5/1990 | Edberg | 435/34 |
| 5,210,022 | 5/1993 | Roth et al. | 435/34 |
| 5,358,854 | 10/1994 | Ferguson | 435/14 |
| 5,364,766 | 11/1994 | Mach et al. | 435/34 |

FOREIGN PATENT DOCUMENTS

| | | |
|---|---|---|
| 0 025 467 A1 | 9/1979 | European Pat. Off. . |
| 0 059 645 A1 | 3/1982 | European Pat. Off. . |
| 0 254 771 A3 | 12/1986 | European Pat. Off. . |
| 3419327 | 5/1984 | Germany . |
| 81010037 | 3/1981 | Japan . |
| 1051078 | 2/1989 | Japan . |
| 2 005 410 A | 9/1978 | United Kingdom . |
| WO 89/04372 | 11/1988 | WIPO . |

OTHER PUBLICATIONS

Brenner et al. (1993) Appl. Envir. Microbiol. 59: 3534–3544.

Brenner et al. App. & Env Microb. v. 59 n. 11, pp.3534–3544 (1993).

D'Aoust, App & Env Microb. v. 35 n.3, pp.483–486, Mar. 1978.

Sartory et al., "A medium detecting β–glucuronidase for the simultaneous membrane filtration enumeration of *Escherichia coli* and coliforms from drinking water", Letters on Applied Microbiology, 1992, 15, pp. 273–276.

Bridson, The Oxoid Manual, "Lauryl Tryptose Broth (Lauryl Sulphate Broth)", 2–124 to 2–125, 6th Ed., 1990, Unipath Ltd., Basingstoke, England.

Enhanced Recovery of Injured *Escherichia coli* by Compounds that Degrade Hydrogen Peroxide or Block its Formation, McDonald, Hackney & Bibey Ray, Applied and Environmental Microbiology, Feb. 1983, pp.360–365,Vol. 45,No.2.

Influence of Diluents, Media and Membrane Filters on Detection of Injured Waterborne Coliform Bacteria, McFeters, Cameron & LeChevallier, Applied and Environmental Microbiology, Jan. 1982, pp.97–103.

Observations on the use of a medium detecting b–glucuronidase activity and lactose fermentation for the simultaneous detection of *Escherichia coli* and coliforms, Letters in Applied Microbiology 1994, 19, pp.47–49, K.S. Walter,E.J. Fricker and C.R. Fricker Jul. 1994.

Canadian Journal of Microbiology, The National Research Council of Canada vol. 23, No. 8,Aug. 1977, A. Hurst, Bacterial Injury: a review.

Hach Products for Analysis Catalog, 1992–1993.

Update: AWWA spearheading move to hasten approval of MMN–MUG test, Journal of the AWWA, p.16, Mar. 1991.

Jermini, Domeniconi and Jaggli, Letters in Applied Microbiology, "Evaluation of C–EC–agar, a modified mFC–agar for the simultaneous enumeration of faecal coliforms and *Escherichia coli* in water samples," p.332–335 1994.

Hurst, Canadian Journal of Microbiology, "Bacterial Injury: A Review," Aug. 1977.

Freier and Hartman,Applied and Environmental Biology, "Improved Membrane Filtration Media for Enumeration of Total Coliforms and *Escherichia coli* from Sewage and Surface Waters," p.1246–1250,Mar. 9, 1987.

"New Medium for the Simultaneous Detection of Total Coliforms and *Escherichia coli* in Water," 1995 Annual Meeting of the American Society for Microbiology, Washington, D.C. May 23, 1995.

(List continued on next page.)

*Primary Examiner*—Lila Feisee
*Assistant Examiner*—Eliane Lazar-Wesley
*Attorney, Agent, or Firm*—Zarley, McKee, Thomte, Voorhees & Sease

[57] ABSTRACT

A selective culture medium which permits simultaneous detection of total coliform and *Escherichia coli* in a test sample with a single growth phase incubation period. The culture medium includes the required components of: (i) carbon nutrients, (ii) a nitrogen nutrient, (iii) a source of metabolizable potassium, (iv) a source of metabolizable phosphate, (v) vitamins, (vi) minerals, (vii) amino acids, (viii) sodium pyruvate, (ix) a bactericidal system selective for non-coliform bacteria which includes methylene blue, erythromycin and an azide, and (x) a sensible indicator selectively metabolized by *Escherichia coli* to the exclusion of other coliforms.

13 Claims, No Drawings

OTHER PUBLICATIONS

Evaluation of Coli ID, a New Chromogenic Medium for Enumeration and Detection of *Escherichia coli* and *Coliforms*, American Society for Microbiology –95th General meeting, Washington, D.C., May 1995.

Frankel, Reitman, and Sonnenwirth; "Gradwohl's Clinical laboratory methods and diagnosis"; vol. 2; 1970; pp. 1111–1113.

Isenberg, Gavan, Smith, Sonnenwirth, Taylor, Maratin, Rhoden, Balows, Collaborative Investigation of the AutoMicrobic System Enterobacteriaceae Biochemical Card, Jun. 1960, p. 694.

Edberg, Trepeta, Kontnick, Torres, Measurement of Active Constitutive BD –Glucosidase (Esculinase) in the Presence of Sodium Desoxycholate, Journal of Clinical, Microbiology, Mar. 1985,p. 363.

Hach *Products for Analysis* 1992–1993 Catalog,p. 1–308

Freier and Hartman; *Improved Membrane Filtration Media for Enumeration of Total Coliforms and Escherichia coli from Sewage and Surface Waters*; Mar. 9, 1987; pp. 1246–1250.

Shadix, Dunnigan, and Rice; *Detection of Escherichia coli by the nutrient agar plus 4–methylumbelliferyl B–D–glucuronide* (*MUG*) *membrane filter method*; Canadian Journal of Microbiology, Sep. 1, 1993;pp. 1066–1070.

Abstracts of the Annual Meeting of the American Society for Microbiology 1984, 84th Annual Meeting,Mar 4–9, 1984, pp. 239–240.

Bailey and Scott's 7th Edition Diagnostic Microbiology, "Methods for Identification of Etiologic Agents of Infectious Disease," pp. 416–418.

Product literature from Austin Biological Labs on "RIM *E. coli* test" .

Product literature from Organon Teknika on "Rapid Detect *E. coli* test system" .

Product literature from Future Medical Technologies on "Qualture™" .

Product literature from RCR Scientific, Inc. on "*redigel*®Colichrome Family" .

Letter to the Editor, Betty H. Olson, Journal AWWA, Feb. 1991.

Minor and Hamida, Annales de L'Institut Psteur, "Advantages of the Demonstration of B–Balactosidase over the Lactose Fermentation in Complex Medium for the Bacterial Diagnosis, Particularly for Diagnostic of Enterobacteriaceae", p. 276.

Buissiere, Foucard, and Colobert; C.R. Acad. Sc. Paris, t.264, "Usage de substrats synthetiques pour l'etude de l'equipe enzymatique de microooganismes", Jan. 9, 1976; pp.415–417.

D'Aoust, "Recovery of Sublethally Heat–Injured Salmonella typhimurium on Supplemental Plating Media," vol. 35, No. 3, pp. 483–486, Mar. 1978.

METHOD AND MEDIUM FOR USE IN DETECTING *E. COLI* AND TOTAL COLIFORMS

CROSS-REFERENCE TO A RELATED APPLICATION

This application is a continuation-in-part of Ser. No. 08/526,865 filed Sep. 12, 1995 now U.S. Pat. No. 5,650,290, which is a continuation-in-part of Ser. No. 08/221,831 filed Apr. 1, 1994, abandoned.

FIELD OF THE INVENTION

The invention relates to the detection of microbes. More specifically, the invention relates to the detection of *Escherichia coli* and total coliforms.

BACKGROUND OF THE INVENTION

Civilization has long recognized the relationship between fecal contamination and the outbreak of disease. Two categories of bacteria routinely tested as indicative of fecal contamination are *Escherichia coli* and total coliforms (typically *Klebsiella sp., Citrobacter sp.*, and *Enterobacter sp.*). Because of the widespread testing for the presence of these two categories of microbial pathogens, substantial effort has been devoted to developing detection systems which permit quick and accurate testing of one or both of these bacterial groups.

Early methods for the detection of coliforms in food and water generally included the steps of (i) inoculating a primary culture medium—formulated to encourage growth of target pathogen(s) while discouraging the growth of others—with a specimen of the food/water to be tested, (ii) incubating the inoculated medium under conditions which promote growth of the target pathogen(s), and then (iii) analyzing the incubated medium to identify and/or quantify the microbes grown on the medium. The specimen introduced into the culture medium may be an untreated sample or a sample which has been treated to concentrate any target microbial pathogens present in the sample—such as by membrane filtration.

The three most common test methods for detecting coliforms are the Multiple Tube Fermentation technique (MTF), the Membrane Filtration technique (MF) and the Presence-Absence technique (P/A). The MTF technique yields the Most Probable Number (MPN), while the P/A technique provides a simple positive/negative answer. In contrast, the MF technique permits direct observation and counting of bacterial colonies. The MFT technique yields results in about twenty-four hours (except for the determination of fecal coliforms which typically requires seventy-two hours) but is difficult to interpret as sample turbidity increases and is typically less precise than MF data.

Because of the difficulty in effectively controlling the growth of other microbial pathogens in culture media, it is frequently necessary to isolate a sample of the suspected target microbial pathogen from the incubated primary culture medium, inoculate a second culture medium with the sample, incubate the second culture medium in order to obtain a purified sample of the microbe, and then test the purified sample to ensure that the suspected target pathogen is—indeed—the target pathogen. The need to conduct a second incubation greatly increases both the time required to conduct the test and the cost of the test.

Various media have recently been developed which include a detection system permitting differentiation of the target bacterial pathogen—such as *Escherichia coli* and/or total coliforms—from other bacteria in the primary medium. Such detection systems include a mechanism by which the target bacterial pathogen(s) is differentiated from other bacteria so as to prevent "false positive readings" while promoting sufficient growth and recovery of the target bacterial pathogen(s) so as to avoid "false negative readings". While simple in theory, formulation of culture media having such dual function detection systems has proven difficult in practice.

The industry has developed several acceptable test methods for detecting *Escherichia coli* and/or total coliforms, but the search continues for superior culture media which can provide quick, accurate and easily readable results.

Examples of the various culture media which have been developed for detecting coliform bacteria and/or *Escherichia coli* are disclosed in International Application WO 89/04372 issued to Berg, European Patent Application Publication 0025467 issued to Rembach, U.S. Pat. No. 4,925,789 issued to Edberg, U.S. Pat. No. 5,210,022 issued to Roth et al., and the journal article New Medium for the Simultaneous Detection of Total Coliforms and *Escherichia coli* in Water by Brenner et al. published in Applied and Environmental Microbiology.

Berg (International Application WO 89/04372) discloses a culture medium formulated to quickly detect the presence/absence of coliforms. The medium includes lactose as a carbon nutrient, a methylumbilliferone substrate as a fluorescent indicator, and the anionic surface active agent sodium lauryl sulfate as a means of accelerating hydrolysis of the methylumbilliferone by the coliforms present in the medium.

A commercially available culture medium—sold under the trademark COLIFASTTM™—is manufactured in accordance with the general precept disclosed in the Berg International Application. Briefly, COLIFAST™ mandates a maximum eight-hour incubation period and is capable of detecting either fecal coliforms or total coliforms, but not both on the same plate.

Rembach (European Patent Application Publication 0025467) discloses a culture medium formulated to detect the presence/absence of *Escherichia coli* which includes the chromogenic substrate 8-hydroxyquinoline glucuronide in combination with X-glucuronide as an activator. Rembach indicates that the medium results in the selective formation of a black precipitate in colonies of *Escherichia coli*.

Edberg (U.S. Pat. No. 4,925,789) discloses a culture medium formulated to detect the presence/absence of a target microbe by limiting the nutrients present in the medium to a nutrient which metabolizes to a unique detectable product (nutrient-indicator) and is capable of being detectably metabolized only by the target microbe. Edberg specifically discloses detection of *Escherichia coli* using a color-indicating nutrient selected from o-nitrophenyl-$\beta$-D-glucuronide (yellow), p-nitrophenyl-$\beta$-D-glucopyranosiduronic acid (yellow), $\beta$-napthalamide-$\beta$-D-glucuronide (purple), $\alpha$-naphthol-$\beta$-D-glucuronide (red) or methylumbilliferyl-$\beta$-D-glucuronide (fluorescent) as the primary nutrient in the medium. Edberg further suggests that the medium may be used to simultaneously test for *Escherichia coli* and total coliforms (EC/TC) by employing different color-indicating nutrients for each of *Escherichia coli* and total coliforms in the medium.

A commercially available culture medium—sold by Environetics under the trademark COLILERT™—is manufactured in accordance with the general precept disclosed in the Edburg '789 Patent. Briefly, the COLILERT™ culture medium detects the presence/absence of *Escherichia coli* and total coliforms (EC/TC) by limiting the nutrients present in the medium to o-nitrophenyl-β-D-galactopyranoside (yellow) which is metabolized by total coliforms and methylumbilliferyl-β-D-glucuronide (fluorescent) which is metabolized to a significant extent only by *Escherichia coli*.

Roth et al. (U.S. Pat. No. 5,210,022) discloses a culture medium formulated to quantify the amount of both *Escherichia coli* and total coliforms in a test sample. The medium limits the primary carbon nutrient in the medium to a chromogenic β-galactosidase substrate producing an insoluble precipitate of a first color when reacted upon by β-galactosidase (produced by coliforms generally) and a chromogenic β-glucuronidase substrate producing an insoluble precipitate of a contrasting color when reacted upon by β-glucuronidase (produced to a significant extent only by *Escherichia coli*). Roth et al. discloses that since the chromogenic indicators are specific to coliforms, the media need not include any inhibitors. While generally effective as an EC/TC testing medium, the medium of Roth requires an incubation period of about 24 to 48 hours and is difficult to read.

A commercial product designed to detect the presence of both *Escherichia coli* and total coliforms in a test sample is sold by RCR Scientific, Inc. under the trademark COLI-CHROME 2. The system is based upon the dual chromogenic and/or fluorescent system disclosed by Roth et al. and includes (i) a chromogenic β-galactosidase substrate which produces a first color when hydrolyzed by β-galactosidase [produced by coliforms generally], and (ii) a chromogenic β-glucuronidase substrate (5-bromo-4-chloro-3-indoxyl-β-D-glucuronide acid cyclohexylammonium salt) which produces a second color when reacted upon by β-glucuronidase [produced to a significant extent only by *Escherichia coli*]. While generally effective as an EC/TC testing medium, the medium suffers from the same limitations as the medium disclosed by Roth et al.

Brenner et al., New Medium for the Simultaneous Detection of Total Coliforms and *Escherichia coli* in Water, Applied and Environmental Microbiology, 59:3535–3544 discloses a culture medium similar to that disclosed in Roth et al. for quantifying the amount of both *Escherichia coli* and total coliforms in a test sample. The medium includes a first chromogenic substrate which produces a fluorescent detectable color when reacted upon by β-galactosidase (produced by coliforms generally) and a second chromogenic substrate producing a second color when reacted upon by β-glucuronidase (produced to a significant extent only by *Escherichia coli*). While generally effective as an EC/TC testing medium, the medium is difficult to read and includes anionic detergents which tend to arrest recovery of stressed coliforms.

As evidenced by the abbreviated discussion set forth herein, several acceptable EC/TC detection systems are available. However, a substantial need continues to exist for quick, accurate and easily readable culture medium which effectively encourages the growth of total coliforms while inhibiting the growth of non-coliforms and provides an observable differentiation between *Escherichia coli* and other coliforms within the medium.

SUMMARY OF THE INVENTION

I have developed a selective culture medium which permits simultaneous detection of total coliform and *Escherichia coli* in a test sample with a single growth phase incubation period. The culture medium includes (i) carbon nutrients, (ii) nitrogen nutrients, (iii) a source of metabolizable potassium, (iv) a source of metabolizable phosphate, (v) vitamins, (vi) minerals, (vii) amino acids, (viii) sodium pyruvate, (ix) a bactericidal system selective against non-coliform bacteria which includes methylene blue, erythromycin and an azide, and (x) a sensible indicator selectively metabolized by *Escherichia coli* to the exclusion of other coliforms.

The culture medium may optionally include (xi) a source of metabolizable magnesium, (xii) sodium chloride as a recovery agent, (xiii) a nonionic surfactant, (xiv) a contrast promoter effective for enhancing the color differentiation between *Escherichia coli* colonies growing in the medium and other bacterial colonies growing in the medium induced by the sensible indicator, and (xv) a highlighting dye for enhancing the visual differentiation of coliform colonies relative to the culture medium.

DETAILED DESCRIPTION OF THE INVENTION INCLUDING A BEST MODE

Definitions

As used herein, including the claims, the term "primary"—when used to describe a component of the medium—means the predominant source for providing the specified attribute, but not necessarily the only source. For example, lactose is the "primary" carbon source in the preferred embodiment of this invention, even though several other components, including the casitone, yeast extract, and 5-bromo-4-chloro3-indolyl-β-D-glucuronic acid cyclohexane salts, also provide metabolizable carbon.

As used herein, including the claims, the term "sodium pyruvate" includes both pyruvic acid ($CH_3$)COCOOH) and sodium pyruvate ($CH_3$)COCOO$^-$Na$^+$).

Composition of Medium

I have developed a selective culture medium which permits simultaneous detection of total coliform and *Escherichia coli* in a test sample with a single growth phase incubation period. The culture medium includes (i) carbon nutrients, (ii) nitrogen nutrients, (iii) a source of metabolizable potassium, (iv) a source of metabolizable phosphate, (v) vitamins, (vi) minerals, (vii) amino acids, (viii) sodium pyruvate, (ix) a bactericidal system selective for non-coliform bacteria, and (x) a sensible indicator selectively metabolized by *Escherichia coli* to the exclusion of other coliforms.

The culture medium may optionally include (xi) a source of metabolizable magnesium, (xii) sodium chloride as a recovery agent, (xiii) a nonionic surfactant, (xiv) a contrast promoter effective for enhancing the color differentiation between *Escherichia coli* colonies growing in the medium and other bacterial colonies growing in the medium induced by the sensible indicator, and (xv) a highlighting dye for enhancing the visual differentiation of coliform colonies relative to the culture medium.

The relative concentrations of components in the medium are selected to provide a pH between 5.0 and 9.0 with a preferred pH of about 7±0.2. This pH favors the growth of coliform bacteria relative to non-coliform bacteria.

A variety of carbon nutrients for supporting coliform growth is available. The most commonly employed carbon nutrient in culture mediums intended to support coliform bacteria is lactose. I have surprisingly discovered that lactose concentrations of greater than about 1 to 2 wt % do not significantly improve coliform growth in the culture and tend to interfere with development of a distinctive red coloration in the coliform colonies. Other components included in the culture medium may also provide carbon nutrients such as the peptones—which are added as a primary source of metabolizable nitrogen.

Similarly, a variety of nitrogen sources suitable for use in the culture medium of this invention are well known and widely available. A widely used nitrogen source which is acceptable for use in the medium of this invention is the peptones, such as casitone. The presence of peptones in the culture tends to aid in the recovery of stressed coliforms. Another suitable nitrogen source is ammonium sulfate.

Metabolizable potassium and phosphate sources are provided to promote bacterial growth. A number of commercially available compounds suitable for use in the medium of this invention are available. A particularly suitable material is potassium phosphate due to its ability to provide effective amounts of both nutrients and buffer the medium against pH shifts caused by metabolism of the nutrients.

A source of vitamins, minerals, and amino acids is also included in the medium. While only small quantities of these compounds are required, they are essential for the coliforms to achieve maximal growth. A readily available source for all of these essential compounds is the widely available commercial preparation known as yeast extract. Yeast extract also contributes a metabolizable source of calcium which is believed to assist in the recovery of stressed coliforms.

Recovery of stressed coliforms is fostered by the inclusion of sodium pyruvate, a well known bacterial protective agent capable of enhancing recovery of coliform bacteria. When incorporated in the present medium, sodium pyruvate has been found to increase bacterial recovery of certain species from ten to one hundred fold. Recovery of stressed bacteria can be further enhanced by the inclusion of a magnesium source, such as anhydrous magnesium sulfate, and a source of sodium, such as sodium chloride, in the medium. Without intending to be limited thereby, it is believed that the presence of magnesium fosters the recovery of stressed coliforms by increasing the strength of the membrane.

The growth of non-coliform bacteria is retarded by the inclusion of a bactericidal system which includes inhibitors selective for non-coliform bacteria. Particularly suitable bactericidal agents which are selective for a broad range of non-coliform bacteria include: dyes such as methylene blue ($C_{16}H_{18}N_3SCl.3H_2O$) and nile blue; azides selective against oxidase positive bacteria; antibiotics such as cefsulodin (a third generation cephalosporin available from Sigma Chemicals), erythromycin (selective against gram positive bacteria), monensin (selective against gram positive bacteria), and penicillin (selective against gram positive bacteria); and nonionic surfactants, such as alcohol $C_{1-4}$ alkoxylates. The growth of non-coliform bacteria is also retarded by selection of an incubation temperature which inhibits growth of the non-coliform bacteria. In addition, certain bacteria simply cannot effectively compete against the coliform bacteria for nutrients and are "starved" by the coliform bacteria present in the medium.

The concentration of azide incorporated into the medium should be carefully monitored due to its ability to adversely impact the recovery and growth of coliform bacteria. I have discovered that a concentration of about 0.005 to about 0.04 g/l azide is effective, in conjunction with the other bactericidal agents, for controlling the growth of non-target bacteria while exhibiting limited effect upon the recovery, growth and development of targeted coliform bacteria.

A nonionic surfactant can be incorporated into the culture medium for purposes of enhancing visibility of the bacterial colonies by increasing colony diameter. Inclusion of a nonionic surfactant also tends to reduce false positive readings—particularly when testing natural water samples—by inhibiting the growth of non-coliform bacteria. Substantially any of the well known nonionic surfactants may be usefully employed in the culture medium of this invention. A detailed list of surfactants is provided in *McCutcheon's; Emulsifiers and Detergents, North American Edition*, Volume 1, 1993. Specific nonionic surfactants suitable for use in the culture medium include the $C_{1-4}$ alkoxylated alcohols, such as the TRITON® X family of octylphenoxy polyethoxy ethanol nonionic surfactants available from Union Carbide Chemical & Plastics Company. The type and amount of surfactant must be carefully selected to limit the bactericidal effect of this component while maximizing the desired characteristics.

Detection of total bacterial colonies incubated on the medium is enhanced by the inclusion of a highlighting dye. The highlighting dye provides a visually perceptible color difference between the medium and the bacterial colonies growing on the medium. Chromogenic substrates which produce a color change when metabolized by coliform bacteria are particularly suitable for this purpose. Chromogenic substrates which are metabolizable by non-coliform bacteria are also suitable as a highlighting dye as the presence of non-coliform bacteria in the medium is controlled by other means. One example of a suitable highlighting dye is triphenyltetrazolium chloride (TTC) which is metabolizable by substantially all bacteria to produce a red pigment. The concentration of TTC incorporated into the medium should be carefully monitored as excessive TTC can inhibit the growth and recovery of coliforms.

A conventional culture medium gelling agent can optionally be included in the medium of this invention as desired. While several solidifying agents are recognized as acceptable for use in gelling culture mediums, agar is generally accepted as the industry standard. Alternatively, the medium can be absorbed in liquid form into sterile pads retained within standard MF-style petri plates.

The detection system of the medium is provided by the inclusion of a sensible indicator which is selectively metabolized by *Escherichia coli* to the exclusion of other coliforms. The selective nature of the indicator permits *Escherichia coli* colonies to be differentiated from colonies of other coliforms and thereby enables detection of both *Escherichia coli* and total coliforms in the same plate. A group of chromogenic substrates selective for *Escherichia coli* are the well known β-glucuronidase substrates. These substrates include a chromogenic moiety attached to a glucuronidase-metabolized moiety wherein the color of the chromogenic moiety is concealed until the metabolizable moiety is cleaved by glucuronidase. Since *Escherichia coli* is the only coliform known to express meaningful quantities of glucuronidase, a bacterial colony in the medium tinted by the chromogenic reagent (based upon the known metabolized color of the reagent) indicates the presence of *Escherichia coli*, while those which are not tinted by the chromogenic reagent indicate the presence of another coliform species. Examples of such selectively metabolizable compounds include specifically, but not exclusively, orthonitrophenyl-β-D-glucuronide (yellow); β-napthalamide-β-D-glucuronide (purple); α-naphthol-β-D-glucuronide (red); methylumbilliferyl-β-D-glucuronide (fluorescent); 5-bromo-4-chloro-3-indolyl-β-D-glucuronic acid cyclohexylammonium salt (blue); 5-bromo-4-chloro-3- indolyl-β-D-glucuronic acid sodium salt (blue), 5-bromo-4-chloro-3-indoxyl-β-D-glucuronide cyclohexylammonium salt (blue); 5-bromo-4-chloro-3-indoxyl-β-D-glucuronide sodium salt (blue); 4-methylumbelliferyl-β-D-glucuronide (fluorescent); 6-chloroindolyl-β-D-glucuronide (mauve or magenta); 4,6-dichloroindolyl-β-D-glucuronide (mauve or magenta); 6,7-dichloroindolyl-β-D-glucuronide (mauve or magenta); 4,6,7-trichloroindolyl-β-D-glucuronide (mauve or magenta); and indoxyl-β-D-glucuronide (blue). The preferred indicator—when the medium is solidified by the inclusion of a solidifying agent or used in conjunction with an absorbent pad—is 5-bromo-4-chloro-3-indolyl-β-D-glucuronic acid cyclohexylammonium salt (often referenced as X-Gluc or BCIG). X-Gluc forms an insoluble precipitate when hydrolyzed by a β-glucuronidase which does not migrate within the medium. This facilitates differentiation of *Escherichia coli* colonies from colonies of other coliforms.

The color differential between *Escherichia coli* colonies and colonies of other coliforms can be intensified by the incorporation of a contrast promoter. Without intending to be limited thereby, it is believed that the contrast promoters described herein achieve an intensified coloration by increasing the formation of glucuronidase by *Escherichia coli*. Promoters particularly suitable for maximizing the formation of glucuronidase by *Escherichia coli* are the essential amino acids of histidine, isoleucine, leucine, lysine, methionine, phenylalanine, threonine, tryptophan and valine.

The medium is capable of promoting and sustaining the growth of coliform bacteria to the exclusion of non-coliform bacteria without the inclusion of an anionic or cationic surface active agent. Ionically active surface active agents are commonly employed in membrane filtration media which include a chromogenic substrate, such as a β-glucuronidase, as they open the bacterial membrane and increase contact between the chromogenic enzymatic substrate and the enzyme produced by the bacteria. Unfortunately, ionically active surface active agents also indiscriminately destroy injured bacteria, resulting in a loss of target bacteria from the inoculated sample. Examples of anionic and cationic surface active agents frequently used in culture media designed for membrane filtration testing include alkyl sulfates such as sodium lauryl sulfate, and bile acids such as deoxycholate and sodium deoxycholate.

A specific formulation found to exhibit the desired bacterial selectivity for coliforms and provide a readily perceived differentiation between *Escherichia coli* colonies and colonies of other coliforms, wherein the preferred concentration is listed in brackets "[ ]", includes:
1. 0.1 to 30 g/l [0.6 g/l] lactose as a carbon nutrient source;
2. 0.01 to 50 g/l [8.0 g/l] of a nitrogen and carbon nutrient containing protein source, such as casitone;
3. 0.001 to 20 g/l [1.25 g/l] monobasic potassium phosphate and 0.002 to 40 g/l [1.75 g/l] dibasic potassium phosphate as metabolizable sources of both potassium and phosphate nutrients;
4. 0.01 to 20 [0.5 g/l] yeast extract as a source of vitamins, minerals and amino acids;
5. 0.01 to 10 g/l [0.3 g/l] anhydrous magnesium sulfate as a metabolizable source of magnesium;
6. 0.01 to 10 g/l [3.0 g/l] sodium chloride as a recovery agent;
7. 0.005 to 40 g/l [1.0 g/l] sodium pyruvate;
8. 0.2 to 10 g/l [0.5 g/l] nonionic surfactant;
9. a bactericidal system selective for non-coliform bacteria of:
    (a) about 0.005 to about 0.04 g/l [0.02 g/l] azide,
    (b) 0.0001 to 0.1 g/l [0.015 g/l] methylene blue, and
    (c) 0.0001 to 0.05 g/l [0.003 g/l] erythromycin;
10. 0.001 to 1.0 g/l [0.2 g/l] 5-bromo-4-chloro-3-indolyl-β-D-glucuronic acid cyclohexylammonium salt as a sensible indicator selectively metabolized by *Escherichia coli* to the exclusion of other coliforms;
11. 0.001 to 20 g/l [0.1 g/l] of an amino acid—such as one or more of the essential amino acids histidine, isoleucine, leucine, lysine, methionine, phenylalanine, threonine, tryptophan and valine—as a contrast promoter for increasing the formation of glucuronidase by *Escherichia coli*; and
12. 0.001 to 0.5 g/l [0.07 g/l] triphenyltetrazolium chloride as a highlighting dye to enhance visual differentiation of coliform colonies from the culture medium.

The medium may optionally include about 0.8 to 2 g/l agar or other suitable thickener to gel the medium in accordance with standard gelling techniques for culture mediums.

The medium is preferably incubated at about 35°±2° C. to encourage the growth of coliforms while discouraging growth of various non-coliforms. Detectable results can often be obtained in about 16 hours with an incubation period of 24±4 hours recommended.

Manufacture of Medium

In a first method of manufacture, the heat treatable components of the medium are mixed together in any order to form a first mixture. The first mixture is autoclave sterilized at about 120° C. for 15 minutes and the sterilized first mixture allowed to cool. The heat labile components of the medium are then mixed together in any order, filter sterilized, and combined with the cooled first mixture to form the culture medium.

In a second method of manufacture, all components of the medium are mixed together and filter sterilized.

Regardless of the method used to manufacture the culture medium, the relative concentrations of the various components in the medium—primarily the concentration of monobasic and dibasic potassium phosphates—are established to provide the medium with a pH of about 7±0.2.

Those components which have limited solubility in water, such as β-glucuronidase 5-bromo-4-chloro-3-indolyl-β-D-glucuronic acid cyclohexylammonium salt and erythromycin, can be dissolved in a minor proportion of an organic cosolvent, such as ethanol, in order to facilitate introduction of the components into the aqueous-based culture medium. The amount of organic cosolvent used should be tightly controlled in order to limit the concentration of organic cosolvent in the final culture medium to less than about 3 wt % with a concentration of less than about 1 wt % preferred.

The heat treatable components present in the preferred composition include (i) the lactose carbon source, (ii) the casitone nitrogen source, (iii) potassium phosphate, (iv) yeast extract, (v) the magnesium source magnesium sulfate, (vi) the nonionic surfactant, (vii) the recovery enhancer sodium chloride, (viii) the methylene blue and azide bactericidal agents, (ix) the amino acids, and (x) agar.

The heat labile components present in the preferred composition include (i) the recovery enhancer sodium pyruvate, (ii) the bactericidal agent erythromycin, (iii) the chromogenic agent β-glucuronidase 5-bromo-4-chloro-3-indolyl-β-D-glucuronic acid cyclohexylammonium salt, and (iv) the highlighting dye triphenyltetrazolium chloride.

The medium is best suited for use in accordance with the membrane filtration technique, but is also suitable for use in accordance with other techniques upon modification of the composition in accordance with standard changes of such media for use in accordance with such other techniques.

If desired, enumeration of total coliform colonies can be confirmed by conducting a confirmatory test for each of the individual coliform colonies identified in the culture medium of the present invention. One example of a suitable confirmatory test is the well known oxidase test which is described in detail in *Standard Methods for the Examination of Water and Wastewater.*

What is claimed is:

1. A culture medium which provides for selective growth of coliforms and simultaneous detection of coliforms and *Escherichia coli* as distinct from other coliforms, and which does so with the use of a chromogenic indicator, to the exclusion of use of any fluorogenic indicators, consisting essentially of:

a media containing a carbon nutrient source, a nitrogen nutrient source, a source of metabolizable potassium, a source of metabolizable phosphate, a source of vitamins, a source of minerals, a source of amino acids, and sodium pyruvate;

a bacterial system selective for non-coliform bacteria which includes methylene blue, erythromycin, and an azide;

a nonionic surfactant for enhancing visibility of bacterial colonies by increasing colony diameter; and a β-glucuronidase substrate selectively metabolized by *Escherichia coli* to the exclusion of other coliforms.

2. A selective culture medium providing simultaneous detection of total coliform and *Escherichia coli* with a single growth phase incubation period comprising:

(a) a carbon nutrient source;

(b) a nitrogen nutrient source;

(c) a source of metabolizable potassium;

(d) a source of metabolizable phosphate;

(e) a source of vitamins;

(f) a source of minerals;

(g) a source of amino acids;

(h) sodium pyruvate;

(i) a bactericidal system selective for non-coliform bacteria which includes methylene blue, erythromycin and an azide; and (j) a β-glucuronidase substrate selectively metabolized by *Escherichia coli* to the exclusion of other coliforms.

3. The medium of claim 2 further comprising a source of metabolizable magnesium.

4. The medium of claim 2 further comprising a recovery agent.

5. The medium of claim 2 further comprising a nonionic surfactant.

6. The medium of claim 2 further comprising a contrast promoter for increasing the color differential between *Escherichia coli* colonies and colonies of other coliforms in the medium selected from the group consisting of histidine, isoleucine, leucine, lysine, methionine, phenylalanine, threonine, tryptophan, valine and mixtures thereof.

7. The medium of claim 2 further comprising a highlighting dye effective for enhancing visual differentiation of coliform colonies from the culture medium.

8. The medium of claim 2 further comprising about 0.8 to about 2 g/l solidifying agent.

9. The medium of claim 2 wherein the pH of the medium is about 6.8 to 7.2.

10. The medium of claim 2 wherein the indicator is selected from the ammonium and sodium salts of 5-bromo-4-chloro-3-indolyl-β-D-glucuronic acid cyclohexane.

11. A selective culture medium providing simultaneous detection of total coliforms and *Escherichia coli* from a single growth phase incubation period comprising:

(k) about 0.1 to 30 g/l lactose, (l) about 0.01 to 50 g/l mixed proteins, (m) about 0.001 to 20 g/l monobasic potassium phosphate, (n) about 0.002 to 40 g/l dibasic potassium phosphate, (o) about 0.01 to 20 g/l yeast extract, (p) about 0.01 to 10 g/l magnesium sulfate, (q) about 0.01 to 10 g/l sodium chloride, (r) about 0.005 to 40 g/l sodium pyruvate as a protective agent, (s) a bactericidal system selective for non-coliform bacteria of:
  1) about 0.0001 to 0.1 g/l methylene blue,
  2) about 0.0001 to 0.05 g/l erythromycin, and
  3) about 0.005 to about 0.04 g/l azide, and
  4) about 0.2 to 10 g/l nonionic surfactant, (t) about 0.001 to 1.0 g/l of an indicator selectively metabolized by *Escherichia coli* to the exclusion of other coliforms selected from the group consisting of the ammonium and sodium salts of 5-bromo-4-chloro-3-indolyl-β-D-glucuronic acid cyclohexane;

(u) 0.001 to 20 g/l methionine for enhancing the formation of glucuronidase by *Escherichia coli* growing in the medium; and (v) 0.001 to 0.5 g/l triphenyltetrazolium chloride as a highlighting dye metabolized by coliforms.

12. The medium of claim 11 further comprising about 0.8 to about 2 g/l agar.

13. A culture medium which provides for selective growth of coliforms and simultaneous detection of coliforms and *Escherichia coli* as distinct from other coliforms, and which does so with the use of a chromogenic indicator, to the exclusion of use of any fluorogenic indicators, consisting essentially of:

a media containing a carbon nutrient source, a nitrogen nutrient source, a source of metabolizable potassium, a source of metabolizable phosphate, a source of vitamins, a source of minerals, a source of amino acids, and sodium pyruvate;

a bacterial system selective for non-coliform bacteria which includes methylene blue, erythromycin, and an azide;

a β-glucuronidase substrate selectively metabolized by *Escherichia coli* to the exclusion of other coliforms; and a recovery agent.

* * * * *